US008698509B2

(12) United States Patent
Call et al.

(10) Patent No.: US 8,698,509 B2
(45) Date of Patent: Apr. 15, 2014

(54) PROXIMITY SENSOR

(75) Inventors: Evan William Call, Bountiful, UT (US); Kent Walker Mabey, West Jordan, UT (US)

(73) Assignee: Roho, Inc., Belleville, IL (US)

(*) Notice: Subject to any disclaimer, the term of this patent is extended or adjusted under 35 U.S.C. 154(b) by 920 days.

(21) Appl. No.: 11/412,859

(22) Filed: Apr. 27, 2006

(65) Prior Publication Data

US 2006/0244466 A1 Nov. 2, 2006

Related U.S. Application Data

(60) Provisional application No. 60/725,901, filed on Oct. 12, 2005, provisional application No. 60/725,006, filed on Oct. 6, 2005, provisional application No. 60/675,315, filed on Apr. 27, 2005.

(51) Int. Cl.
*G01R 27/26* (2006.01)

(52) U.S. Cl.
USPC .......................................... 324/661; 324/662

(58) Field of Classification Search
USPC ........ 324/661, 662, 663, 671, 644; 73/862.68
See application file for complete search history.

(56) References Cited

U.S. PATENT DOCUMENTS

| | | | |
|---|---|---|---|
| 3,747,952 A | 7/1973 | Graebe | |
| 4,239,415 A | 12/1980 | Blikken | |
| 4,541,136 A | 9/1985 | Graebe | |
| 4,833,457 A | 5/1989 | Graebe, Jr. | |
| 4,907,845 A | 3/1990 | Wood | |
| 5,526,701 A | 6/1996 | Tamori | |
| 5,640,728 A | 6/1997 | Graebe | |
| 5,853,005 A | 12/1998 | Scanlon | |
| D415,567 S | 10/1999 | Bar | |
| D415,834 S | 10/1999 | Bar | |
| D416,326 S | 11/1999 | Bar | |
| 6,014,602 A * | 1/2000 | Kithil et al. | 701/45 |
| 6,025,782 A | 2/2000 | Newham | |
| 6,034,526 A | 3/2000 | Montant | |
| 6,067,019 A | 5/2000 | Scott | |
| 6,154,907 A | 12/2000 | Cinquin | |
| 6,165,142 A | 12/2000 | Bar | |
| 6,297,738 B1 | 10/2001 | Newham | |
| 6,337,602 B2 | 1/2002 | Hilliard et al. | |

(Continued)

OTHER PUBLICATIONS

Fink, Standard Handbook for Electrical Engineers, McGraw Hill, 1968, $10^{th}$ edition, p. 10-152 . . . 10-155 and 20-8 . . . 20-9.*

(Continued)

*Primary Examiner* — Thomas F Valone
(74) *Attorney, Agent, or Firm* — Polster Lieder Woodruff & Lucchesi, L.C.

(57) ABSTRACT

An immersion sensor for use with a cushion or mattress for determining the relative immersion of a person within the cushion or mattress including a sensor, a ground and a circuit for measuring capacitance. The sensor includes a sheet of conductive material, and the ground includes a second sheet of conductive material. The circuit is adapted to send short bursts of electrical current to the sensor and a capacitor. The circuit is further adapted to measure the length of time the burst of current takes to charge the capacitor. Based upon the measured time, the circuit calculates the proximity of the object based upon the time taken to charge the capacitor. A method that may be implemented with the immersion sensor is also disclosed.

46 Claims, 17 Drawing Sheets

(56) References Cited

U.S. PATENT DOCUMENTS

| | | | |
|---|---|---|---|
| 6,356,187 B2 * | 3/2002 | Jinno et al. | 340/438 |
| 6,367,106 B1 | 4/2002 | Gronsman | |
| 6,385,803 B1 | 5/2002 | Viard | |
| 6,445,988 B1 | 9/2002 | Breed et al. | |
| 6,457,355 B1 | 10/2002 | Philipp | |
| 6,466,036 B1 | 10/2002 | Philipp | |
| 6,487,738 B1 | 12/2002 | Graebe | |
| 6,517,106 B1 | 2/2003 | Stanley et al. | |
| 6,552,550 B2 * | 4/2003 | Karray et al. | 324/662 |
| 6,623,080 B2 | 9/2003 | Clapper | |
| 6,772,639 B2 | 8/2004 | Seals | |
| 6,778,090 B2 | 8/2004 | Newham | |
| 6,825,765 B2 * | 11/2004 | Stanley et al. | 340/561 |
| 6,840,100 B1 | 1/2005 | Wotiz | |
| 6,885,306 B2 | 4/2005 | Holzman et al. | |
| 6,897,661 B2 | 5/2005 | Allen et al. | |
| 6,940,291 B1 | 9/2005 | Ozick | |
| 7,017,642 B2 * | 3/2006 | Brahler, II | 157/1.17 |
| 7,098,674 B2 * | 8/2006 | Stanley et al. | 324/662 |
| 7,583,199 B2 | 9/2009 | Graebe, Jr. | |
| 2003/0233136 A1 | 12/2003 | Williams | |
| 2004/0012056 A1 | 1/2004 | Nejad | |
| 2004/0083550 A1 | 5/2004 | Graebe, Jr. | |
| 2004/0113634 A1 | 6/2004 | Stanley et al. | |
| 2004/0177449 A1 | 9/2004 | Wong et al. | |
| 2005/0200489 A1 | 9/2005 | Sloop | |

OTHER PUBLICATIONS

U.S. Appl. No. 11/064,534, filed Feb. 24, 2005, David J. Sloop et al.
Capacitive Sensors Design and Applications by Larry K. Baxter, IEEE Press 1997, Chapter 6, pp. 66-82.
Search Report for International Application No. PCT/US2006/016195.
Written Opinion of the PCT for International Application No. PCT/US2006/016195.

\* cited by examiner

PROXIMITY SENSOR

RELATED APPLICATIONS

The present application claims priority to U.S. Provisional Application Ser. No. 60/725,901 filed Oct. 12, 2005, U.S. Provisional Application Ser. No. 60/725,006 filed Oct. 6, 2005, and also U.S. Provisional Application Ser. No. 60/675,315 filed Apr. 27, 2005. The contents of said applications are hereby incorporated by reference.

FIELD OF THE INVENTION

The invention relates to proximity sensors. More specifically, the invention relates to a sensor for detecting a relative distance of an object to the sensor by detecting changes in charge transfer.

BACKGROUND OF THE INVENTION

Proximity sensors for detecting an actual or relative distance between the sensor and an object are known in the art. For example, U.S. Pat. No. 6,621,278 to Arie Ariav discloses a method of measuring a distance by transmitting a cyclically-repeating wave. The wave is then received at a second location in the medium. The system detects a predetermined point in the cyclically-repeating wave that is received at the second location and continuously changes the frequency of transmission of the cyclically-repeating energy wave in accordance with the detected point of each received cyclically-repeating wave received at the second location such that the number of waves received at the second location is a whole integer. The change in frequency to produce a measurement of the predetermined parameter is used to determine the distance the wave has traveled. However, this system has drawbacks, particularly in that the sensor is unduly complex both in electronic implementation and in sensor construction.

Other types of detectors, primarily for detecting the presence or absence of an object, use ultrasonic and radio frequency transmitters and detectors that receive reflected energy when an object is present in an area of interest. These detectors however cannot be used practically to detect a relative or actual distance, particularly in very short distances. In certain settings, the amount of RF energy generated by these types of device is unacceptable due to interference. Moreover, some people have concerns about constant exposure to RF energy.

Many applications require low power consumption and detection of a relative distance within a range of interest. For example, cushions for wheelchairs must be inflated to a pressure that is sufficient to properly immerse the person in the cushion to prevent the formation of decubitus ulcers on the person in the wheelchair. However, often the people bound to the wheelchair do not have the ability to feel when they are properly immersed in the cushion, such as a paraplegic or quadriplegic person. For those people, others must periodically check the person's immersion within the cushion to ensure the person is not in an overinflated state, such that only a small portion of the person's body is bearing their weight, or in an underinflated state, such that the person has "bottomed out" and is no longer supported entirely by the cushion. Similarly in a cushion not inflated with air, problems also exist when determining the proper cushion immersion. However, presently, no acceptable means of detecting the immersion of a person in a cushion exists. Only indirect measurement of pressure internally in the cushion is available. This type of measurement is dependant upon the materials of construction and structural conformation all creating significant limitations in the applicability of the measurement.

Likewise, people bound to hospital beds must avoid decubitus ulcers when confined to the bed for long periods of time. To accomplish this, inflation mattresses are commonly used, and the inflation level of the mattress must be monitored in order to maintain the proper inflation level to prevent overinflation or underinflation of the mattress. Moreover, because the person's weight is concentrated over their entire back side, multiple locations must be checked for underinflation or overinflation. As a result, a sensor which is divided into zones to check the immersion of the patient within the mattress is needed.

SUMMARY OF THE INVENTION

The present invention comprises an immersion sensor for use with a cushion or mattress for measuring the depth of immersion of a person within the cushion or mattress comprising a sensor, a ground and/or shield and a circuit for measuring capacitance. The sensor comprises a sheet of conductive material, and the ground comprises a second sheet of conductive material. The circuit is adapted to send short bursts of electrical current to the sensor and the reference capacitor. The circuit is further adapted to measure the length of time the burst of current takes to charge the capacitor. Based upon the measured time, the circuit calculates the proximity of the object based upon the time taken to charge the capacitor. The present invention also comprises a method that may be implemented with the immersion sensor.

DESCRIPTION OF THE PREFERRED EMBODIMENT

Figure 1:
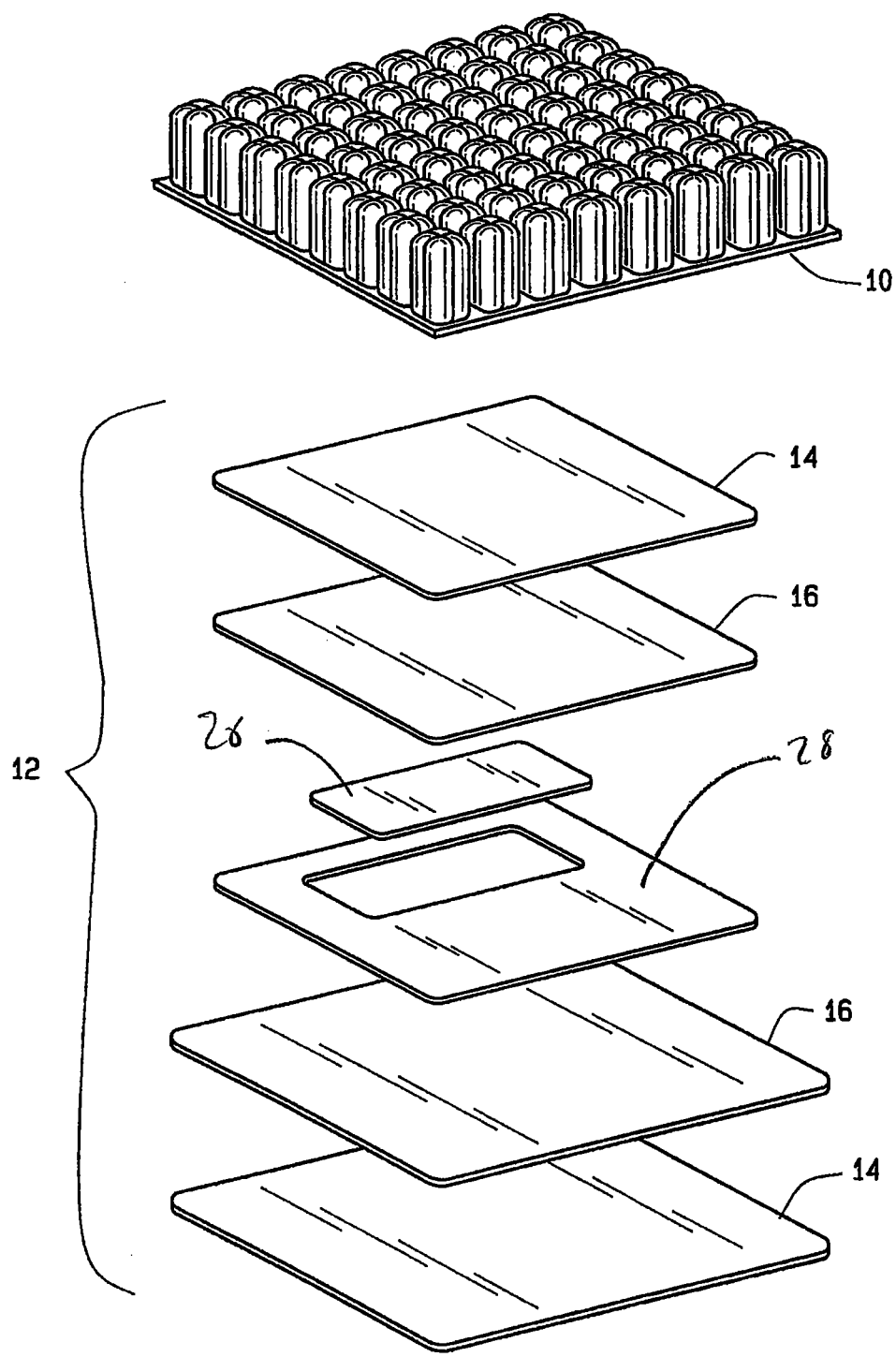
FIG. 1 is an exploded perspective view of a wheelchair cushion proximity detection device according to an embodiment of the present invention.

While this invention is susceptible of embodiment in many different forms, there is shown in the drawings and will herein be described in detail preferred embodiments of the invention with the understanding that the present disclosure is to be considered as an exemplification of the principles of the invention and is not intended to limit the broad aspect of the invention to the embodiments illustrated.

The preferred embodiment of the present invention is a proximity sensor that utilizes charge transfer measuring technology and large-area capacitive sheets to determine the distance of an object from the capacitive sheet. The charge transfer measurement is employed with a short, low duty cycle burst of power. Burst mode permits power consumption in the low microamp range, thereby dramatically reduces radio frequency (RF) emissions, lowers susceptibility to electromagnetic interference (EMI), and yet permits excellent response time. Internally, it is preferred that the signals are digitally processed to generate the required output signals. The charge transfer measurement device switches and charge measurement hardware functions are preferably all internal to the charge transfer measurement device.

To that end, the invention will be described, by way of example and not by limitation, in reference to a cushion for a wheelchair. Referring to FIG. 1, there is shown an inflatable cushion 10, for example the cushion described in U.S. Pat. No. 4,541,136. Placed below the cushion is a sensor 12 according to the present invention to detect the immersion of a person within the cushion. The sensor 12 comprises two exterior sheets of neoprene rubber 14. Sandwiched between the sheets of rubber are thin layers of foam 16 and between the thin layers of foam 16 is a sensor area 26 and a grounding plane area 28.

Figure 2:
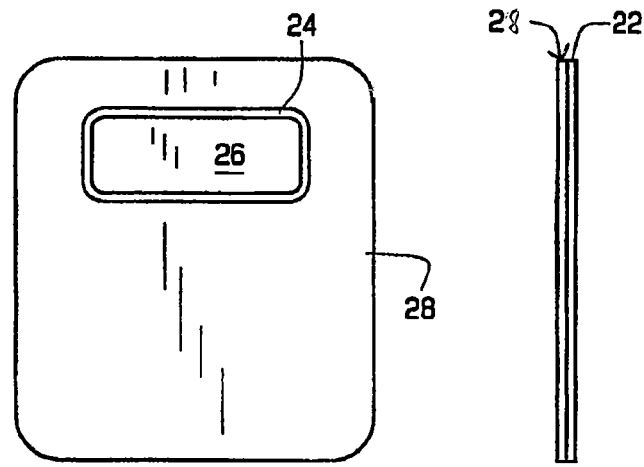
FIG. 2 is a plan view of the conductive and nonconductive layers of the proximity detection device according to an embodiment of the present invention.

The sensor layer 18 of FIG. 2 comprises a conductive sheet 20 adhered to a nonconductive sheet 22. The conductive sheet 20 is preferably made from copper, and the nonconductive sheet 22 is preferably made from a polyester film. The sensor layer 18 may also be made from any other conductive material, such as a conductive polymer. The conductive sheet 20 when made from copper preferably has a thickness of about 0.0005 of an inch. The conductive sheet 20 is interrupted, preferably by etching or die cutting, along an area 24 to form a sensor area 26 and a grounding plane area 28. The ratio of the upper surface area of the grounding plane area 28 to the upper surface area of the sensor area 26 is about 8:1. While the sensor layer 18 is described as copper and polyester sheets, the nonconductive sheet is not required and may be omitted and the conductive sheet may be made from any conductive material, such as a conductive braid, mesh or screen printing a conductive material onto a nonconductive base. Additionally, while the sensor area 24 is shown as rectangular, the sensor area 26 may be appropriately shaped and located in order to provide the optimum geometry to the object to be sensed. In the example of FIG. 2, the sensor area is confined to a rear portion of the sensor where a person's buttocks would be located when seated in the wheelchair. Since most of a person weight is distributed in this location while seated, this located is at the greatest danger of bottoming out. However, it is within the scope of the present invention to provide a sensor at any location or multiple locations of the seating area.

Figure 3:
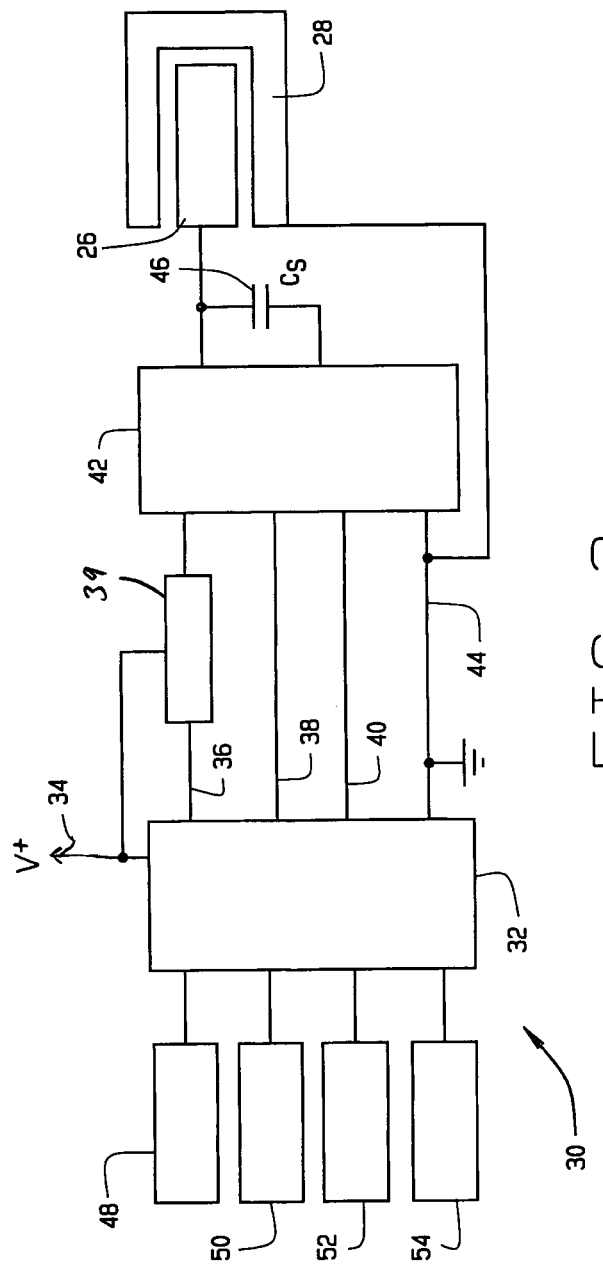
FIG. 3 is a diagram of a circuit according to an embodiment of the present invention.
Figure 5A:
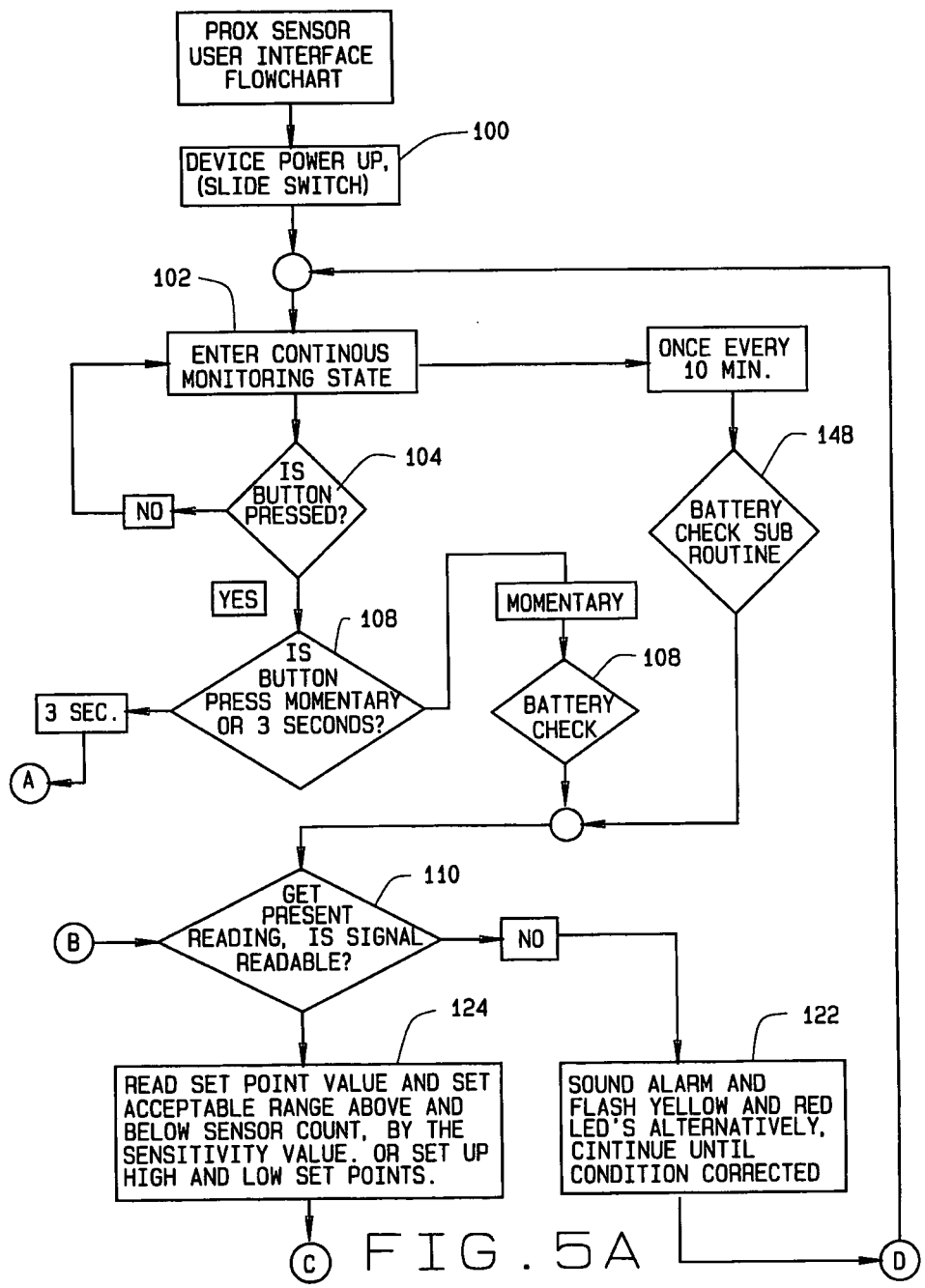
FIGS. 5A-5D are a flow chart showing the operation of the hardware and software of the circuit of FIG. 3.
Figure 5B:
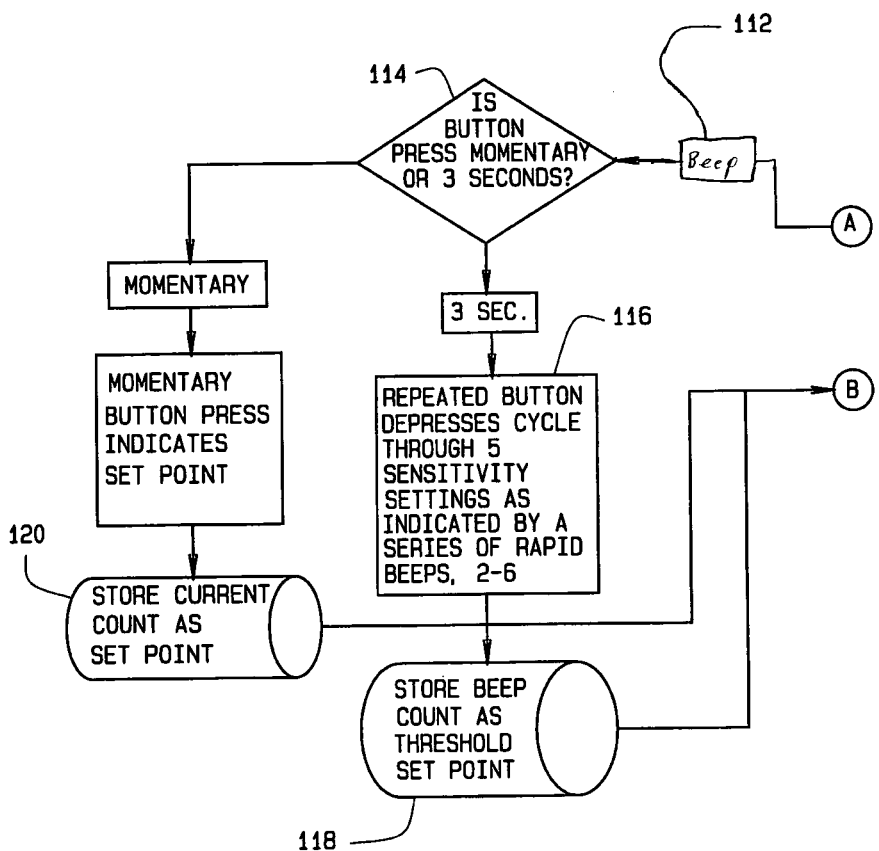
Figure 5C:
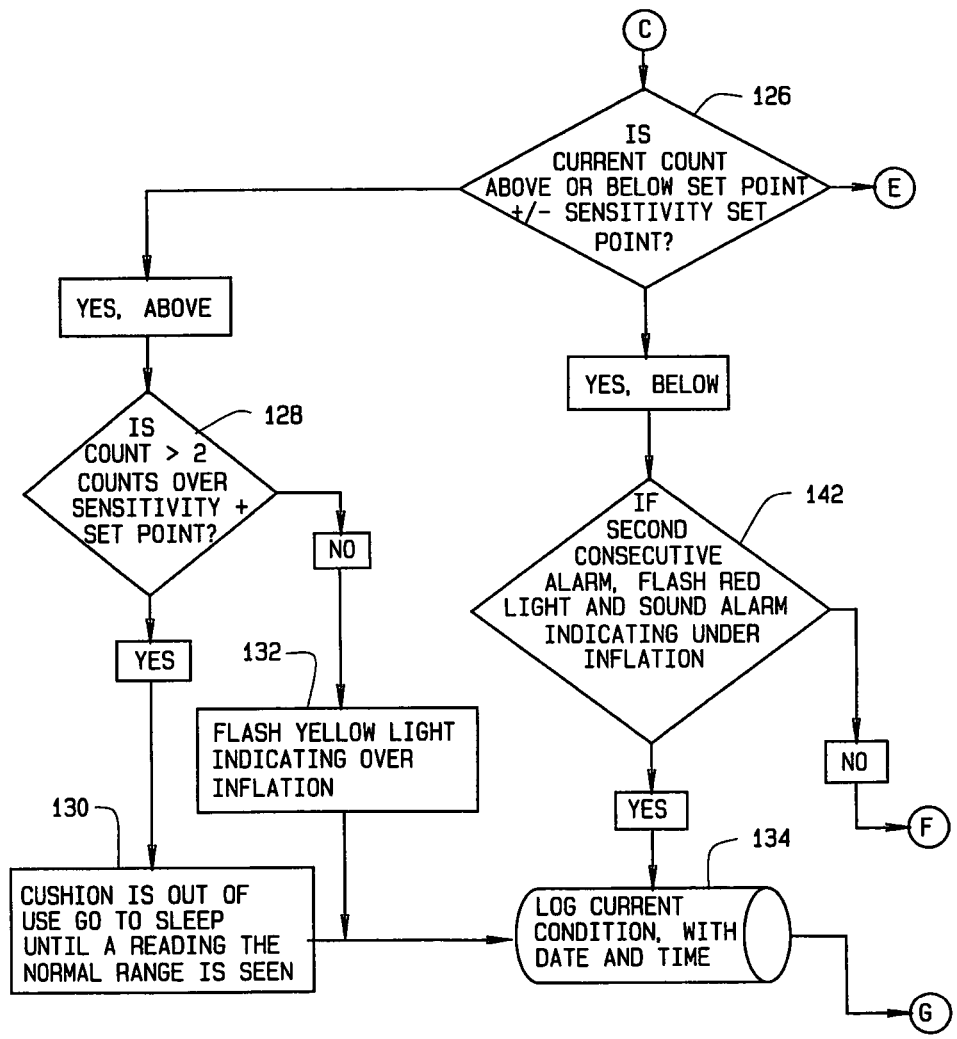
Figure 5D:
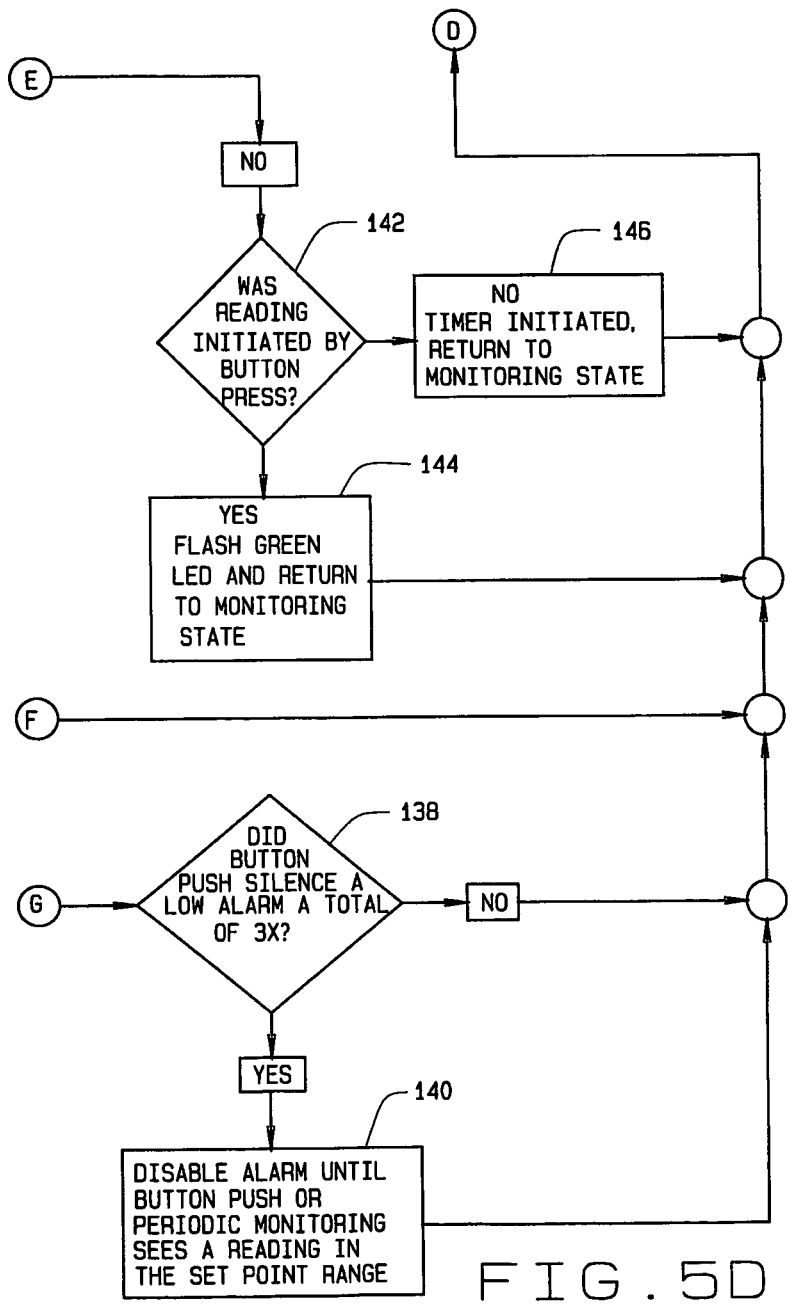

The problem solved by the ground layer with using charge transfer or capacitive technology with wheel chair cushions is that there is no good ground to use as reference. The grounding plane area 39 being in the area around the sensor area 26 allows a capacitance measurement to be made relative to the distance between the person and the sensor and ground areas 26 and 28. The present invention is attached to a circuit 30 as shown in FIG. 3. The circuit generally comprises a microcontroller 32, such as a 16LF818 available from Microchip Technology, Inc. of Chandler, Ariz. The microcontroller 32 is powered by a 3.5 volt battery 34. Attached to the enable line 36 of the microcontroller 32 is a voltage regulator 39 for regulating the input voltage to the microcontroller 32. Attached to the clock line 38 and the data line 40 is a charge transfer sensor 42. The data line 40 transmits data from the charge transfer sensor 42 to the microcontroller indicating the distance of an object, in this case a person's buttocks, from the sensor area 26. The data is preferably in the form of a hexadecimal number representative of the relative distance of the person from the sensor area. In the preferred embodiment, the charge transfer sensor 42 is a QProx QT117 available from Quantum Research of Hamble, Southampton, United Kingdom. A ground line 44 is also connected to the charge transfer sensor 42, as well as to the grounding plane 28. The capacitive sensor 42 also requires a capacitor 46, having a capacitance $C_s$, attached to two lines of the sensor 42. The capacitance of the capacitor 46 is preferably 0.022 µF and a temperature stable dielectric such as COG, but such value will change based upon the size and the application of the sensor.

Also attached to the microcontroller 32 are various outputs to alarms and indicators 48, inputs from an on/off switch 50 and an operator input switch 52, and inputs from other controls 54, such as if the circuit 30 is used as a feedback loop to automatically control the inflation of the cushion, as described below.

Figure 4:
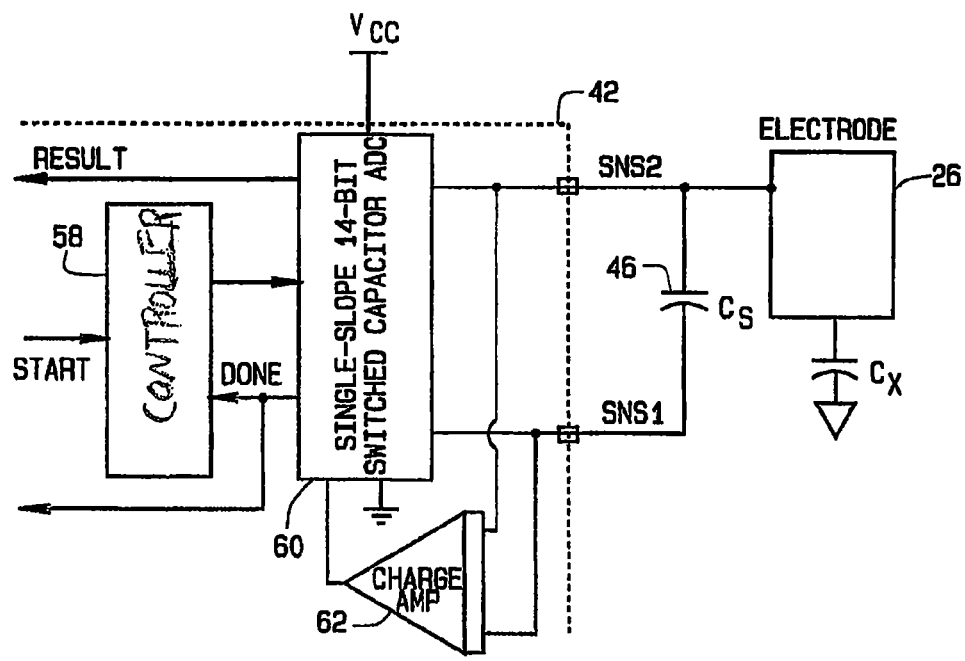
FIG. 4 is a diagram of a circuit of a charge transfer device according to an embodiment of the present invention.

Referring to FIG. 4, the charge transfer sensor 42 employs a short, low duty cycle burst of charge-transfer cycles with a burst controller 58 and amplifier 62 to acquire its signal. Internally the signals are digitally processed with an analog to digital converter (ADC) 60 to generate the required output signals. The charge transfer sensor 42 switches and charge measurement hardware functions are all internal to the sensor 42. The ADC 60 is 14-bit single-slope switched capacitor ADC including both the required sensor 42 charge and transfer switches in a configuration that provides direct ADC conversion. The burst length is inversely proportional to the rate of charge buildup on the capacitor 46 ($C_s$), which in turn depends on the values of $C_s$, $C_x$ (the load capacitance of the sensor) and $V_{cc}$. $V_{cc}$ is used as the charge reference voltage. Larger values of $C_x$ cause the charge transferred into $C_s$ to accumulate more rapidly. As a result, the values of $C_s$, $C_x$ and $V_{cc}$ should be fairly stable over the expected operating temperature range.

The internal ADC 60 treats $C_s$ as a floating transfer capacitor. As a direct result, the sensor 26 can be connected to either SNS1 or SNS2 with no performance difference. The polarity of the charge buildup across $C_s$ during a burst is the same in either case. $C_s$ must be of within a certain range for proper operation. It is important to limit the amount of stray capacitance on both terminals, especially if the load $C_x$ is already large, for example by minimizing trace and wire lengths and widths so as not to exceed the $C_x$ load specification and to allow for a larger sensing electrode size if so desired. The circuit board traces, wiring, and any components associated with or in contact with SNS1 and SNS2 will become proximity sensitive and should be treated with caution.

The microcontroller 32 operates according to the flow chart of FIG. 5. In a first step, the device is powered on 100 and enters a continuously monitoring state 102. From this state, the microcontroller 32 monitors whether an input operator input switch 52 has been depressed in decision step 104. If it is has not, the microcontroller 32 returns to the monitoring state 102. If the switch 52 has been depressed, the next step is to determine whether the depression was for three seconds or less in decision step 106. If for three seconds or less, the battery health is checked in step 108 and a present reading of the distance of the person from the sensor area 26 is determined in step 110.

If a button 52 is determined to have been pressed greater than three seconds in step 106, then in step 112, the microcontroller 32 causes an alarm 48 to beep momentarily and proceeds to step 114 where the circuit again determines of the button 52 has been depressed for more than three more seconds. If so, the microcontroller 32 cycles through a series of five sensitivity settings as indicated to the user by a rapid succession of beeps of the alarm 48 in step 116. The sensitivity setting is then stored in step 118 and the circuit continues to step 110 to read the present distance.

If in step 114 it is determined that the button 52 has not been depressed for an additional three seconds, a value indicating the present distance is stored as the preferred set point in step 120, and the circuit sounds an alarm and continues to step 110 to read the present distance.

If in step 110, the present value of the distance of the person from the sensor area 26 is not readable, the circuit continues to step 122 and flashes yellow and red LEDs alternatively. If the value is readable, the microcontroller 32 continues to step 124 and sets a tolerance above and below the current setpoint which will be considered within acceptable range from the setpoint. Next, in step 126, the microcontroller 32 decides whether the present reading is within range or above or below range.

If the reading is above range, in step 128, the microcontroller 32 determines whether the current reading is greater than or equal to two counts over the previously chosen and stored sensitivity plus the setpoint. If the condition is true, the microcontroller 32 proceeds to step 130 where the microcontroller 32 determines it is not presently being used and goes to sleep until a reading is in the normal range. If the condition is not true, the microcontroller 32 flashes a yellow LED 48 to indicate that the cushion is overinflated. In either event, the microcontroller 32 next optionally proceeds to step 134, where it logs the current condition date and time. If the embodiment is not one in which the data indicating inflation status is logged, the microcontroller will proceed to step 136.

In step 136, if the current reading is below the acceptable range, the microcontroller will flash the red LED 48 and sound an audible alarm 48 to indicate underinflation if the current reading is the second consecutive reading to determine underinflation and proceeds to step 134.

After step 134, the microcontroller 32 determines whether a user has pushed the button 52 to silence the audible alarm 48 in step 138. If yes, the microcontroller 32 proceeds to step 140 and disables the audible alarm 48 until a second button push or a current sensor reading shows a reading with the acceptable range. After steps 138 and 140, the microcontroller 32 proceeds to step 102.

If it is determined in step 126 that the setpoint is within the acceptable range, the microcontroller 32 continues to step 142 where the microcontroller 32 determines if the present reading was initiated by a button 52 press. If yes, in step 144 the green LED 48 is flashed and the microcontroller 32 returns to the monitoring state in step 102. If no, in step 146, the microcontroller 32 reinstates the timer and return to step 102.

Returning back to step 102, if in the monitoring state ten minutes have elapsed, the microcontroller 32 will initiate a current reading automatically by proceeding to step 148 by performing a battery check and proceeding to step 110.

Figure 6:
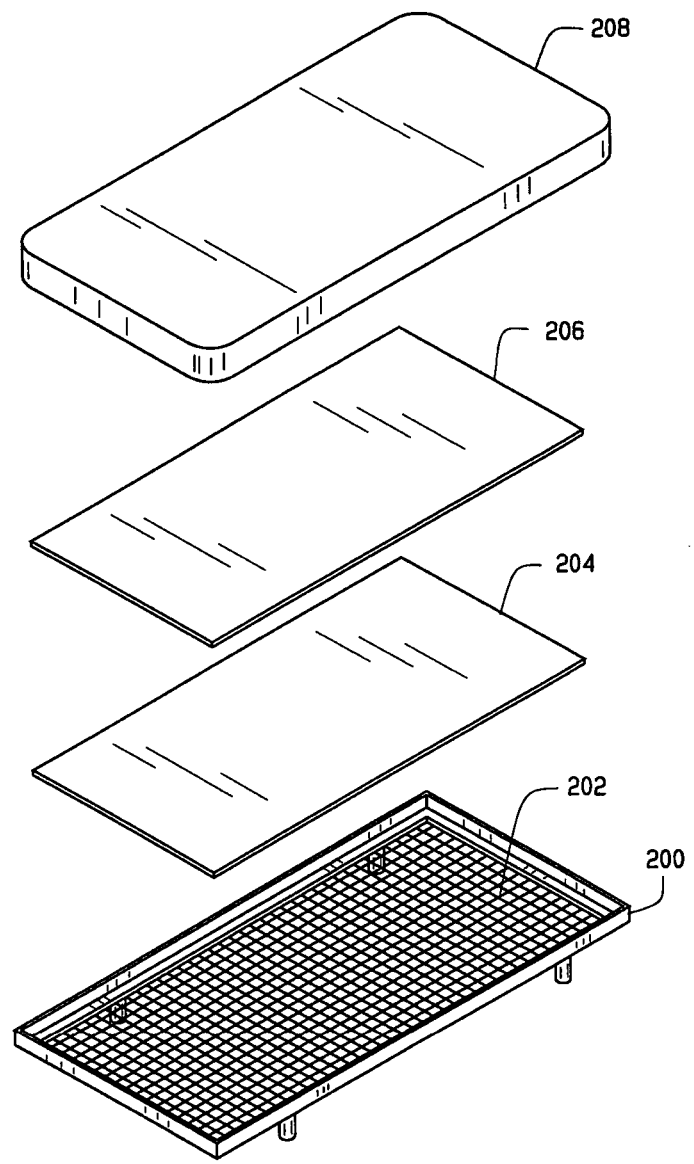
FIG. 6 is an exploded perspective of a proximity detector for a bed air cushion according to an embodiment of the present invention.

As another example shown in FIG. 6, the sensor can be used in a hospital bed to determine whether a patient has bottomed out when using an inflatable air mattress. In this instance, the bed comprises a bed frame 200 comprising a spring support 202. Placed upon the spring support are a shield plane 204 and a sensor plane 206. Upon the sensor plane 206 is placed an air mattress 208. The shield plane 204 acts to isolate the metallic items of the bed 200, particularly the spring support 202, from the sensor plane 206. The sensor plane 206 in its simplest application comprises a single sheet of conductive material, as with the previously discussed embodiment. The driven shield isolates the metal items of a bed and chair below the sensor plane 206. In a device without a driven shield the effect of surrounding metal is subtracted by the user creating a setpoint based on the desired immersion level and the relative reading observed at that immersion.

Just as with the wheelchair cushion proximity detector, the circuitry 30 operates in the same manner except that the shield plane 204 is driven to provide isolation from the metallic structure of the bed. The distance between the sensor plane 206 and the shield plane 204 is preferably about ⅛" to about ⅜". A problem posed by the hospital bed situation is the amount of metal in the bed and mattress support structure. The driven shield under the sensor or sensor area in the case of multiplexed units (described below) shields the sensor plane 206 in that direction of the location of the shield plane 204 giving increased sensitivity in the desired direction and ignoring changes in conductive materials and noise generating devices with position changes of the relative position of the device with the bed or other devices.

Figure 7:
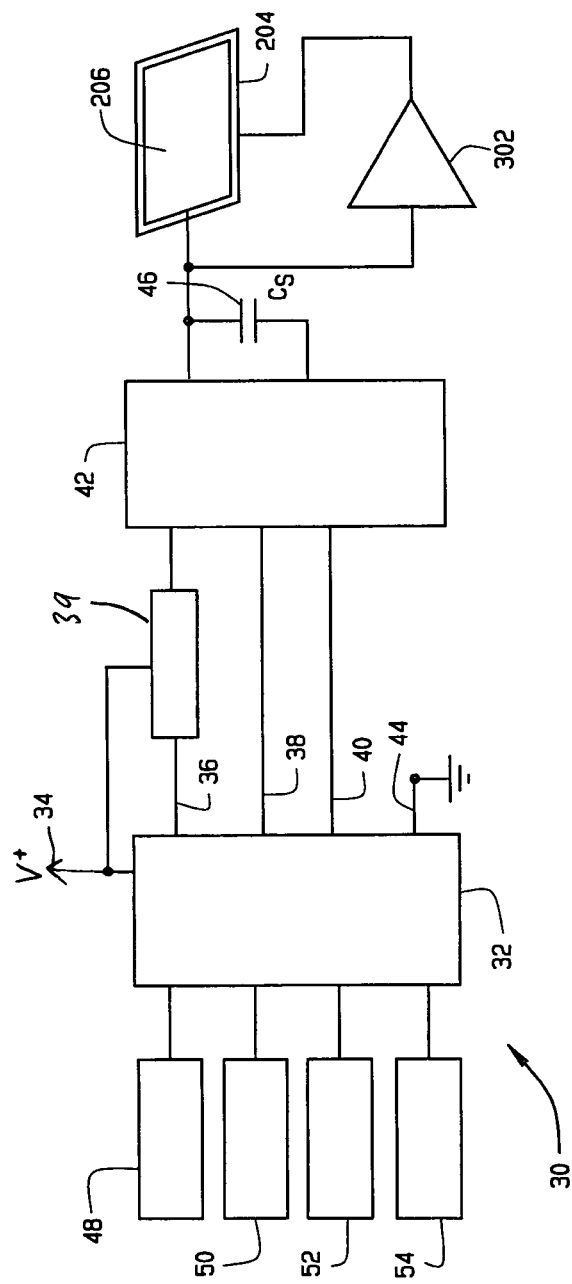
FIG. 7 is a diagram of a circuit according to another embodiment of the present invention.

In this regard and referring to FIG. 7, the original circuit 30 is modified to form circuit 30'. The numerals of circuit 30' that correspond to circuit 30 are unchanged. However, the circuit 30 further comprises an amplifier 302 which is driven from an output of the charge transfer sensor 42 and serves to drive the shield plane 204 to isolate the sensor plane 206 from the metal portions of the bed 200.

Figure 8:
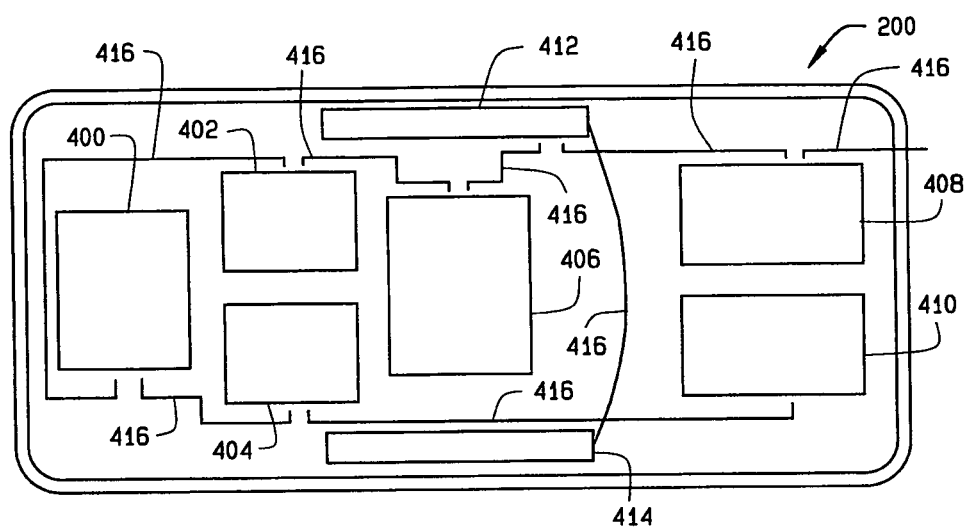
FIG. 8 is a diagram of a sensor placement on a bed cushion proximity detector according to an embodiment of the present invention.

In another embodiment shown in FIG. 8, the bed 200 may be equipped with multiple sensors 400-414 in the sensor plane 206. For example, the first sensor 400 would be placed in the area of the patient's head, two more sensors 402 and 404 in the area of a patient's shoulders, yet another sensor 406 in the area of the patient's buttocks, and finally two more sensors 408 and 410 in the area of the patient's feet. Entrapment sensors 412 and 414 are also located near the bed rails to provide an indication that the patient has rolled to one side of the bed and has possibly become entrapped in the railing.

The sensors 400-414 are all conductively attached to a charge transfer sensor to form a single sensor plane 206. The shield plane 204 is similarly divided into portions that correspond to the size and the shape of the sensors 400-414. The result is that one charge transfer sensor 42 is required for each sensor 400-414.

Figure 9:
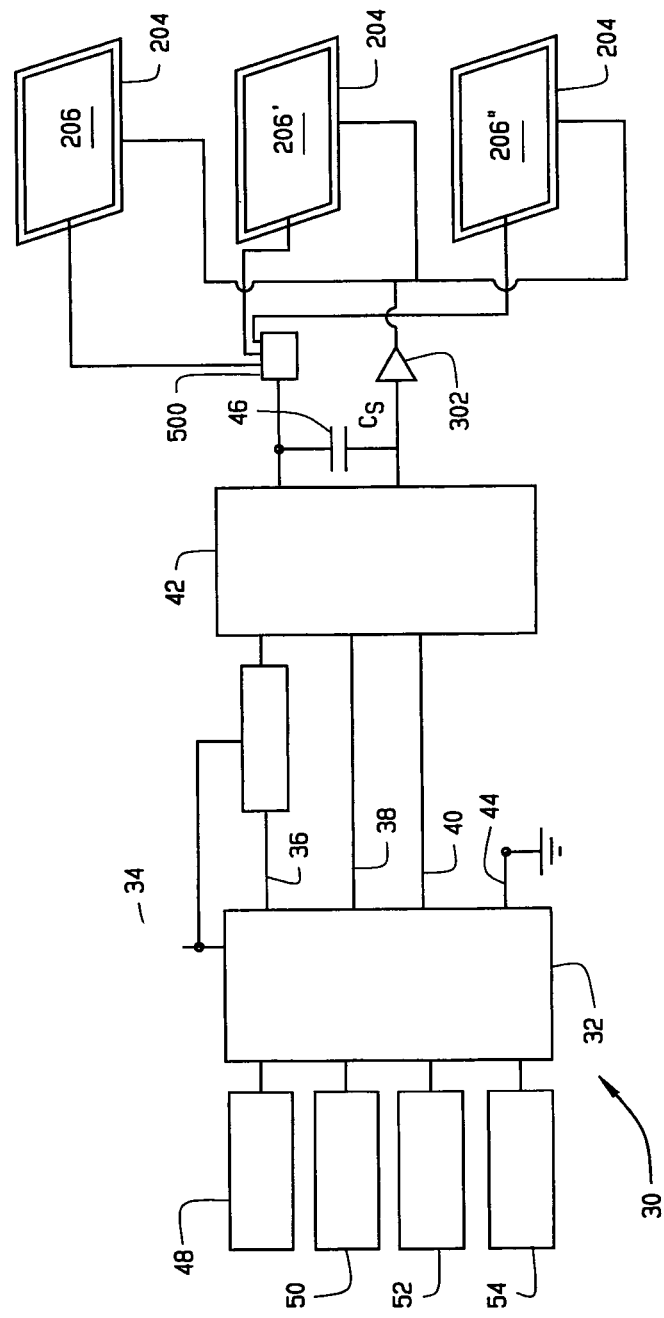
FIG. 9 is a diagram of a circuit according to another embodiment of the present invention.
Figure 17:
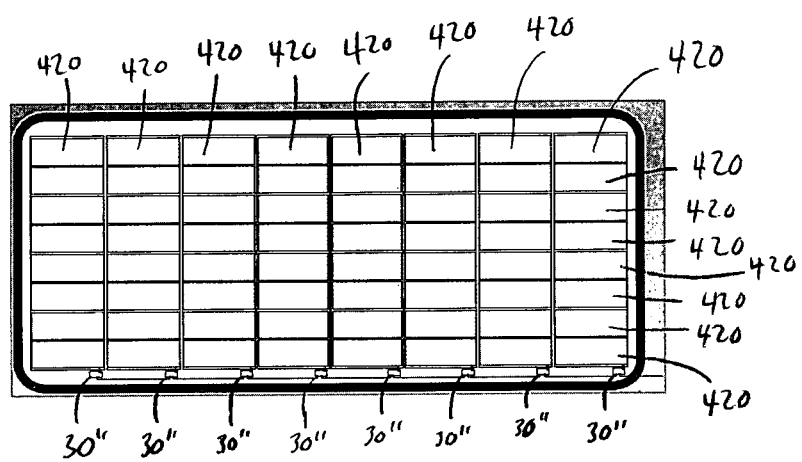
FIG. 17 is a diagram of a sensor placement on a bed cushion proximity detector according to yet another embodiment of the present invention.

To provide the ability to monitor an even greater number of sensors, a circuit 30" as shown FIG. 9 can be implemented. The circuit is identical to the circuit 30' except that a multiplexer 500 is inserted between the output of the charger transfer sensor 204 and a plurality of sensors 206, 206' and 206". The multiplexer 500 switches from sensor 206 to sensor 206' to sensor 206", in turn, in order to determine the distance of the relevant portion of the lying person from the sensors 206, 206', 206". In this manner, only one circuit 30" is required to poll a multiplicity of sensors 400-414. Because of timing limitations of available charge transfer sensors, a limited number of sensors can be daisy chained. Also, due to stray capacitance issues the number of sensors that can be reasonably multiplexed, a combination of multiplexed and daisy chained sensors may be implemented in order to maximize the number of sensors. Thus, for example, sixty-four sensors may be implemented by arranging the sensors as eight daisy chains of sensors multiplexed to the circuits 30" with each chain having eight sensors 420, as shown in FIG. 17.

Figure 10:
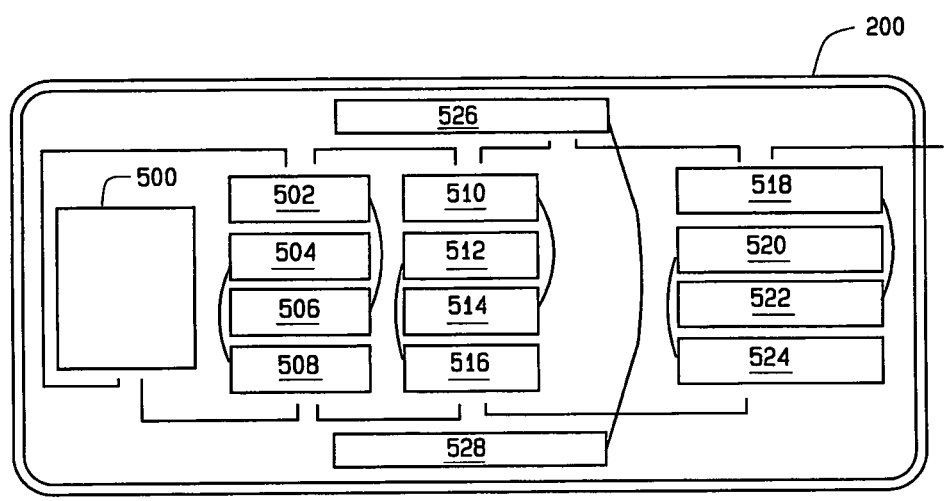
FIG. 10 is a diagram of a sensor placement on a bed cushion proximity detector according to yet another embodiment of the present invention.

In that regard and referring to FIG. 10, an embodiment is shown wherein thirteen sensors 500-524 are provided which determine the patient's immersion within the air cushion and two more sensors 526 and 528 are provided that determine whether the patient has become entrapped in the bed rails. These sensors 500-528 may be either daisy chained, attached to their own circuits or multiplexed. Moreover, a combination of daisy chaining sensors and multiplexing sensors may be performed.

Figure 11:
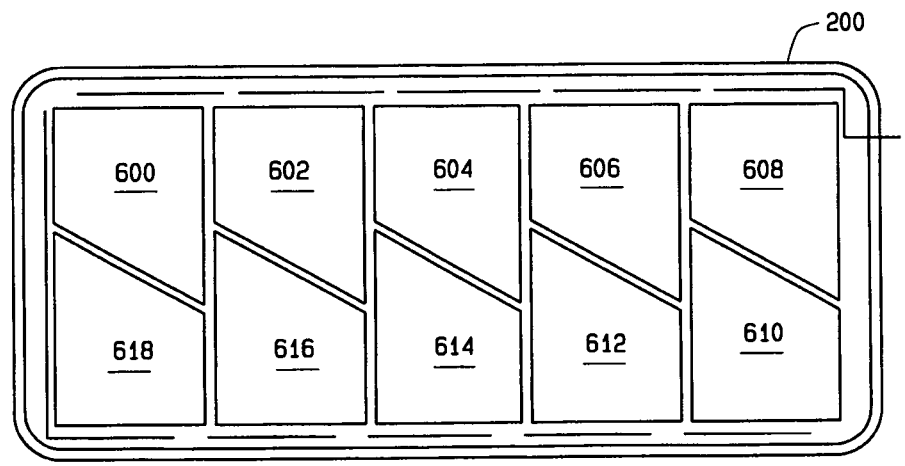
FIG. 11 is a diagram of a sensor placement on a bed cushion proximity detector according to yet another embodiment of the present invention.

In FIG. 11, yet another embodiment is shown wherein the coverage area of the bed is higher, but with fewer sensors 600-610. This arrangement may be more appropriate for monitoring not whether a person is properly immersed, but rather if they are present or absent from their bed. Such an application would be useful in hospitals and nursing homes. Again, these sensors 600-610 may be either attached to their own circuits or multiplexed.

Figure 12:
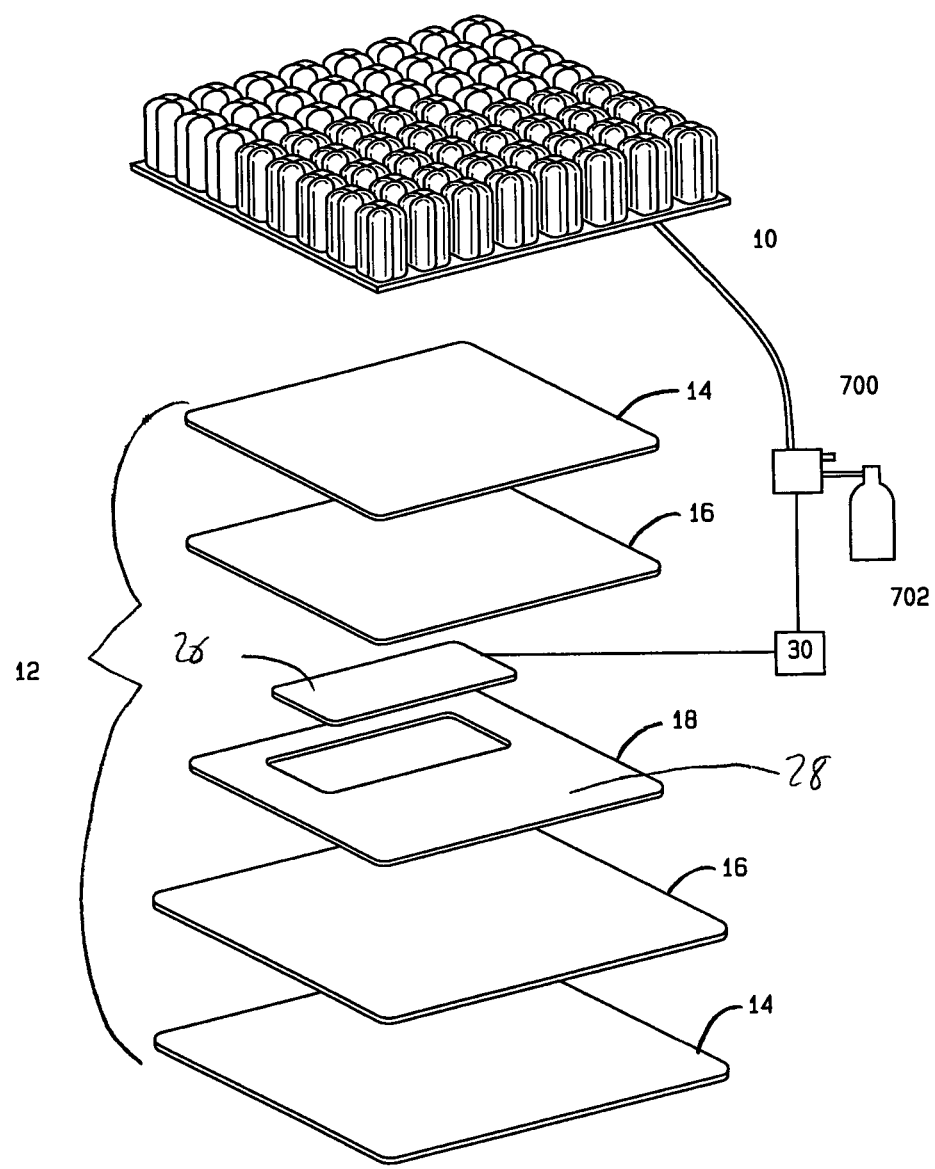
FIG. 12 is an exploded perspective view of an automatically adjusting wheelchair cushion according to an embodiment of the present invention.

Another application for the present invention defined in the claims is for use as a feedback loop in the auto-inflation or auto-deflation of a cushion for wheelchair. Referring to FIG. 12, such an embodiment is shown. Specifically, an output of the microcontroller 32 notifies a valve 700 to change positions to add air, release air or remain closed based upon the inflation status of the cushion 10. The valve 700 is attached to a source of compressed air 702, which supplies compressed air when an underinflation status is detected. Likewise, when an overinflation status is detected the valve 700 slowly releases air from the cushion 10 until the proper inflation level is achieved. Similarly, in a low air loss cushion for a hospital bed the circuit may similarly serve as a feedback loop to control mattress inflation, such as by providing feedback to a bed blower control.

Figure 13:
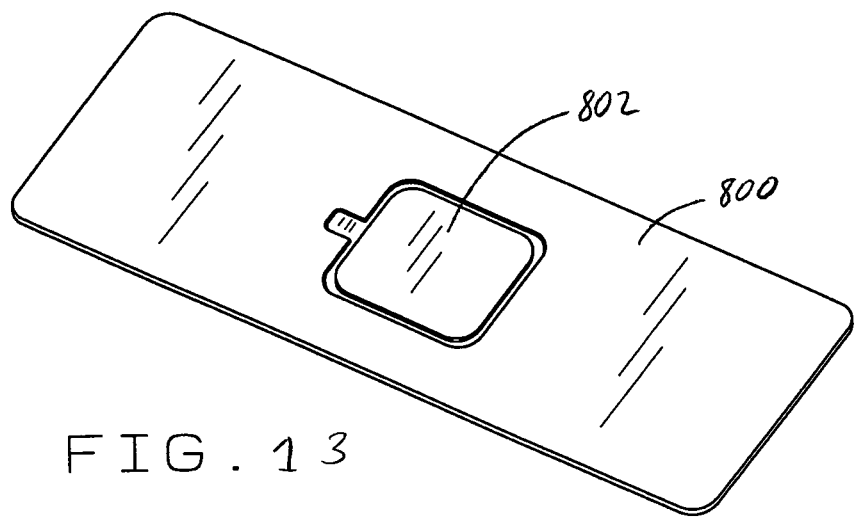
FIG. 13 is a perspective view of an embodiment of the device including a first sensor of relatively large area and a second sensor of relatively small surface area according to an embodiment of the present invention.

In the embodiments shown above, it is necessary to manually "teach" the microprocessor the extents of the travel by indicating the microprocessor the extents of proximity of the detected object. In that manner, the microprocessor can determine a relative proximity of the detected object within the known range. In the embodiment of FIG. 13, the device may comprise a sensor within a sensor.

In this embodiment, there is provided a first sensor 800 comprising a large area with respect to a second, smaller sensor 802. In the embodiment of FIG. 13, the second, smaller sensor 802 is surrounded by the first, larger sensor 800. Below the first and second sensors 800 and 802, and electrically isolated therefrom, is a ground plane 804 and a driven shield The first sensor 800 is made fairly large to anticipate contact points over a surface of interest (for example, the area under a person's buttocks in a wheelchair cushion application). The large sensor 800 gives a reading of charge transfer that is highly dependant on the size of the individual above the sensor. As a result, without manually setting the range of extents of travel of the person in the wheelchair cushion example, it is difficult to determine the precise proximity of a person of unknown size.

Merely by way of example, a large person may range between a value of 76 and 120 at the extents of travel of that person's proximity to the sensor 800. A small person may range between values of 100 and 150 at their extents of proximity. Therefore, at the closest extent of travel, a large person may show a reading of 76 and the small person may show a reading of 100 making it difficult to determine the proximity of a person of unknown size.

However, the charge transfer of only the small sensor 802 is not as dependent on the size of the person above of the sensor. This is because the area of the sensor is small in relation to the person above the sensor. Unfortunately, however, the small sensor 802 cannot monitor a large area of interest.

Figure 15:
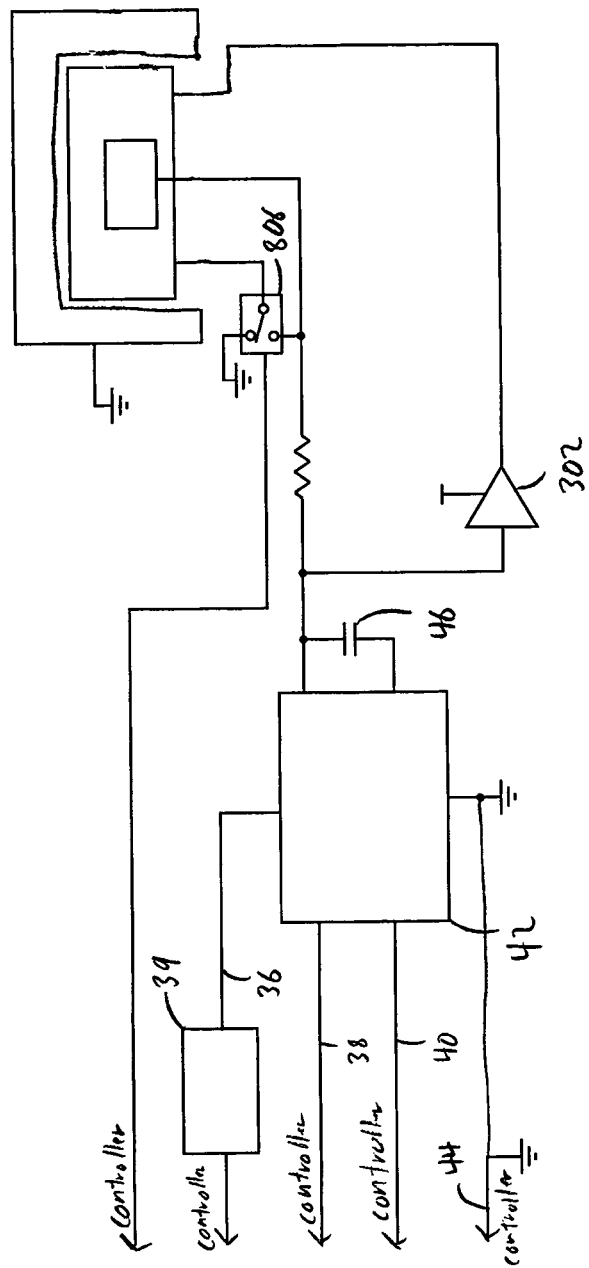
FIG. 15 is a diagram of a circuit for operating the embodiment of FIG. 14.

In the embodiment of FIG. 13, the multiplexer or switch 806 (FIG. 15), for example a single pole double throw analog switch such as the FSA3157 available from Fairchild Semiconductor of South Portland, Me., is used to alternately electrically connect the charge transfer sensor 42 to either the small sensor 802 or to both the large sensor 800 and the small sensor 802. The microcontroller 32 may then read the proximity value of the small sensor 802 and determine, over the small area, the relative proximity of the object above. Next, the large sensor 800 and the small sensor 802 are electrically connected to the charge transfer sensor 42 and the proximity value of the object of interest will be determined. By correlating this value to the value determined by the small sensor 802, the range of values of proximity for the large sensor 800 and small sensor 802 together can be determined based upon the present value for the small sensor 802. Alternatively, rather than using the value of the small sensor 802 to correlate with the value of the large sensor 800 and small sensor 802 together, the value of the large sensor 800 alone could be detected and correlated with the value small sensor 802 to obtain a proximity value over only the large sensor's 800 area.

Additionally, when sensing the proximity value of the small sensor 802, it is desirable to electrically connect the large sensor 800 to the ground plane 804. This is accomplished by using a control line from the microcontroller that controls the switch 806 and connects the peripheral sensor area either ground or part of the sensor. Alternatively, this may also be accomplished by utilizing the frame output of the charge transfer device to make a logic switch after the first reading each time the device is powered up.

Figure 14:
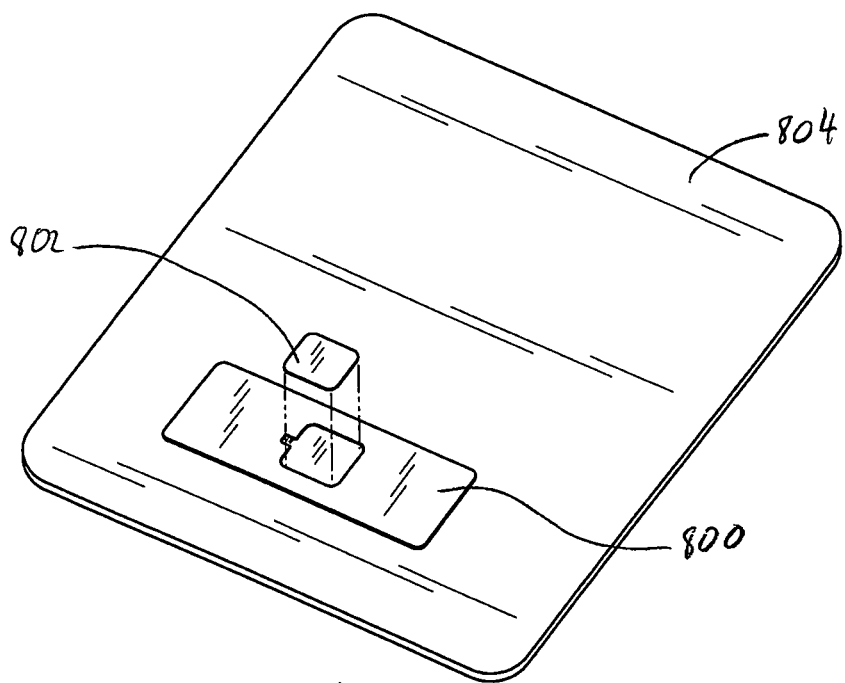
FIG. 14 is a perspective view of an embodiment of the device including a first sensor of relatively large area and a second sensor of relatively small surface area with a ground plane according to an embodiment of the present invention.

While the embodiment of FIGS. 13 and 14 is shown having a driven shield and a ground plane, it will be appreciated by one of ordinary skill in the art that an embodiment not having the driven shield may also be implemented without departing from the scope of the present invention.

Figure 16:
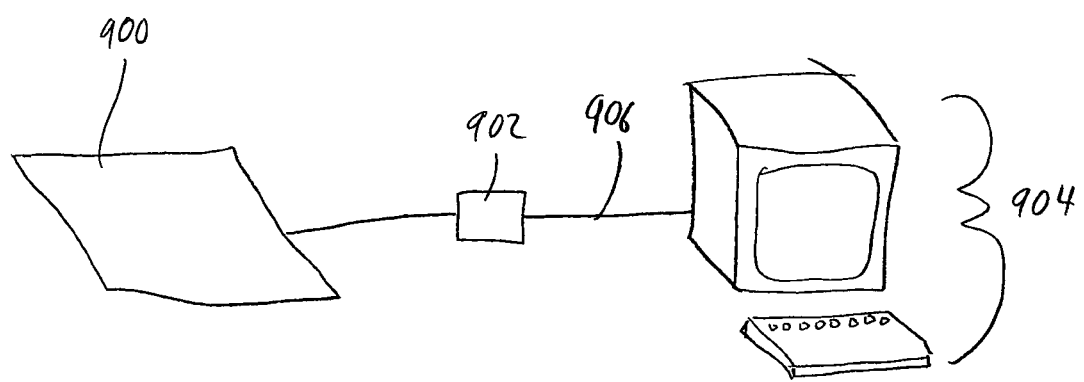
FIG. 16 is diagram of an embodiment of the present invention including a visual display device.

Referring to FIG. 16, another embodiment of the present invention provides a visual display for graphically representing a relative proximity value for a sensor or group of sensors. In this embodiment, the sensor array and its associated microcontroller 32 of FIG. 14 (shown in FIG. 16 as reference numeral 900) is electrically connected to a reader device 902, which comprises a circuit board that provides an interface between the sensors and microcontroller 32 and a display device 904, which in the preferred embodiment is a computer.

The reader device 902 preferably connects to the display device 904 via a USB cable 906. The display device 904 runs a program which continuously reads the digital value of each sensor in the array, and represents those values graphically. The reader device 902 is not required to be a separate unit. Its functionality could be incorporated into either the sensor circuit or the display device 904.

Because the sensors are not calibrated, and because the actual digital value for a particular proximity level is influenced by a number of factors (such as sensor size, shape, and material, and mattress or cushion density and thickness), the display device 904 should provide a method of correlating the actual digital values with proximity levels for each sensor, for each particular system. For example, it can provide a table of maximum and minimum values for each sensor. The maximum value is set to the actual digital value that results from a proximity level of infinity (a body in farthest proximity), and the minimum value is set to the actual value that results from a proximity level of zero (a body in nearest proximity). Then, the digital values within the maximum and minimum range are translated and displayed more meaningfully as proximity values. These values are determined and entered manually, or by way of an auto-range mode in the display device. In this mode, it would monitor the digital values for each sensor, and automatically adjust the table entries as it observes new maximum and minimum values, and as a technician provides appropriate near and far stimulus to each sensor.

While the invention is described above as separate devices used in conjunction with a hospital bed or wheelchair cover, the devices may be integrally formed with the wheelchair cushion or hospital mattress or with the wheelchair or hospital bed without departing from the scope of the present invention.

Other applications for the proximity sensor would be as a bed/chair occupancy detector to notify hospital or nursing home attendants as to the presence or absence of the patients from a bed or chair. Similarly, it could serve as a toilet seat occupancy device for notifying when a disabled patient has been left on a toilet seat for too long. Moreover, it may be used for car seat occupancy detection to control air bag deployment in a crash. Another application would be for seat occupancy detection on an airplane.

There are several veterinary applications for the invention as well. For example, before giving birth horses will lay down in their stall. Horse breeders will typically keep a close eye on a horse about to give birth. In order to ease the burden of checking on the horse, a sensor can be placed in the floor of the stall. When the animal lies down, the breeder would be notified by the circuit to attend to the horse. Additionally, it could be used in horse trailers to monitor the horse.

It could similarly be used on a person as a geriatric fall monitor. The sensor would be placed on the person's body and when proximity with the floor was detected, an alarm for help automatically sounded. Possible locations would be on the person's hip or shoulder.

Finally, if the conductive layer were placed in close proximity contact with the torso, it could be used to monitor patient vital signs, such as respiration and heartbeat.

The above examples show that the invention, as defined by the claims, has far ranging application and should not be limited merely to the embodiments shown and described in detail. Instead the invention should be limited only to the explicit words of the claims, and the claims should not be arbitrarily limited to embodiments shown in the specification. The scope of protection is only limited by the scope of the accompanying claims, and the Examiner should examine the claims on that basis.

We claim:
1. An immersion sensor assembly comprising:
a cushion or mattress having an adjustable depth of immersion;
a sensor comprising a conductive material;
a ground comprising a second conductive material electrically isolated from the sensor and surrounding the sensor;
a circuit comprising a reference capacitor, the circuit adapted to send short bursts of electrical current to the sensor and the reference capacitor, the circuit adapted to measure the length of time the burst of current takes to charge the reference capacitor and the circuit adapted to calculate the proximity of a person based upon the time taken to charge the reference capacitor; and
wherein the circuit is adapted to provide an indication when the person is too deeply immersed within the cushion or mattress.

2. The immersion sensor assembly of claim 1 further comprising at least one layer of nonconductive material disposed over the sensor and ground.

3. The immersion sensor assembly of claim 2 wherein the nonconductive material is foam.

4. The immersion sensor assembly of claim 1 wherein the sensor is disposed within a protective encasement of neoprene rubber.

5. The immersion sensor assembly of claim 1 wherein the assembly is integrally formed with a cushion.

6. The immersion sensor assembly of claim 1 wherein the assembly is integrally formed with a mattress.

7. The immersion sensor assembly of claim 1 wherein the circuit comprises a microprocessor and a capacitive sensor.

8. The immersion sensor assembly of claim 1 wherein the planes formed by the sensor and the ground, when the assembly is laid flat, are nominally parallel.

9. The immersion sensor assembly of claim 1 further comprising a driven shield to isolate the sensor from the effect of electromagnetic interference or metallic objects in the direction of the driven shield from the sensor.

10. The immersion sensor assembly of claim 1 wherein the sensor comprises a plurality of sensors and the ground provides a plurality of grounds.

11. The immersion sensor assembly of claim 10 wherein the circuit is attached to two or more of the plurality of sensors to simultaneously determine the proximity of people to each of the sensors.

12. The immersion sensor assembly of claim 10 wherein the circuit comprises a multiplexer, the multiplexer being attached to two or more of the sensors and also to the circuit and adapted to selectively connect the sensors to the circuit.

13. The immersion sensor assembly of claim 1 further comprising a second sensor comprising a conductive material covering an area smaller than the first sensor.

14. The immersion sensor assembly of claim 13 wherein the circuit is adapted to obtain a proximity measurement from the second sensor to determine a scale of proximity for proximity measurements from the first sensor.

15. An immersion sensor for use with a cushion or mattress for measuring the depth of immersion of a person within the cushion or mattress comprising:
a sensor layer comprising a conductive material;
a ground layer comprising a second conductive material electrically isolated from the sensor and at least partially surrounding the sensor, the ground layer electrically connected to and maintained at a ground electrical potential;

a circuit comprising a reference capacitor, the circuit adapted to send short bursts of electrical current to the sensor layer and the reference capacitor, the circuit adapted to measure the length of time the burst of current takes to charge the reference capacitor and the circuit adapted to calculate the proximity of the person based upon the time taken to charge the reference capacitor; and wherein the sensor layer and the ground layer, when the immersion sensor is laid flat, are nominally coplanar.

16. An immersion sensor assembly comprising:
a cushion or mattress having an adjustable depth of immersion;
a sensor comprising a sheet of conductive material;
a ground layer surrounding the sensor layer;
a shield comprising a second sheet of conductive material located adjacent to and having generally the same shape and area as the sensor;
a circuit for detecting the capacitive effect of a person upon on the cushion or mattress and providing a relative output for a microcontroller; and
wherein the circuit is adapted to provide an indication when the person is too deeply immersed within the cushion or mattress.

17. The immersion sensor assembly of claim 16 further comprising at least one layer of nonconductive material disposed over the sensor.

18. The immersion sensor assembly of claim 17 wherein the nonconductive material is foam.

19. The immersion sensor assembly of claim 16 wherein the sensor is disposed within a neoprene rubber encasement.

20. The immersion sensor assembly of claim 16 wherein the device is integrally formed with a cushion.

21. The immersion sensor assembly of claim 16 wherein the device is integrally formed with a mattress.

22. The immersion sensor assembly of claim 16 wherein the planes formed by the sensor and the shield, when the immersion sensor is laid flat, are nominally parallel.

23. The immersion sensor assembly of claim 22 wherein the sensor comprises a plurality of sensors and the shield is sized to isolate the plurality of sensors.

24. The immersion sensor assembly of claim 23 wherein the circuit is attached to two or more of the plurality of sensors to simultaneously determine the proximity of people to each of the sensors.

25. The immersion sensor assembly of claim 24 wherein the circuit comprises a multiplexer, the multiplexer being attached to two or more of the sensors and also to the circuit and adapted to selectively connect the sensors to the circuit.

26. A method of determining the proper immersion of a person within a cushion or mattress comprising the steps of:
providing a sensor layer below the cushion or mattress comprising a sheet of conductive material;
providing a ground layer that is nominally coplanar to the sensor layer and is held at a constant ground potential;
using the sensor layer to sense the proximity of the person to the sensor layer to determine the person's immersion within the cushion or mattress; and
generating a signal when the person is either overimmersed or underimmersed within the cushion or mattress.

27. A method of determining the proper immersion of a person within a cushion or mattress comprising the steps of:
providing a first sensor below the cushion or mattress comprising a sheet of conductive material;
providing a ground layer comprising a sheet of conductive material that is nominally coplanar and maintained at a ground potential below the cushion or mattress;
sending short bursts of electrical current to the sensor and a capacitor;
measuring the length of time the burst of current takes to charge the capacitor;
calculating the proximity of the person based upon the time taken to charge the capacitor; and
providing an indication when the person is either overimmersed or underimmersed within the cushion or mattress.

28. The method of claim 27 further comprising the step of providing a ground comprising a second sheet of conductive material adjacent the first sensor.

29. The method of claim 27 further comprising the step of providing a shield layer comprising a sheet of conductive material and driving the shield to isolate the sensor from the effect of stray capacitance and electromagnetic interference.

30. The method of claim 27 further comprising the steps of:
providing a second sensor of smaller area than the first sensor comprising a second sheet of conductive material;
sending short bursts of electrical current to the second sensor and the capacitor;
measuring the length of time the burst of current takes to charge the capacitor; and
calculating the proximity of the person based upon the time taken to charge the capacitor; and
determining a scale for the calculation from the first sensor from the calculation obtained from the second sensor.

31. A method of determining the proper immersion of a person within a cushion or mattress comprising the steps of:
providing a sensor comprising a sheet of conductive material positioned below the cushion or mattress;
providing a ground comprising a second sheet of conductive material that surrounds the sensor;
sending short bursts of electrical current to the sensor and a capacitor;
measuring the length of time the burst of current takes to charge the capacitor;
calculating the proximity of the person based upon the time taken to charge the capacitor; and
providing an indication when the person is either overimmersed or underimmersed within the cushion or mattress.

32. The method of claim 31 further comprising the step of providing a shield layer comprising a sheet of conductive material and driving the shield to isolate the sensor from the effect of stray capacitance and electromagnetic interference.

33. The method of claim 31 further comprising the steps of:
providing a second sensor of smaller area than the first sensor comprising a second sheet of conductive material;
sending short bursts of electrical current to the second sensor and the capacitor;
measuring the length of time the burst of current takes to charge the capacitor; and
calculating the proximity of the person based upon the time taken to charge the capacitor; and
determining a scale for the calculation from the first sensor from the calculation obtained from the second sensor.

34. An immersion sensor assembly comprising:
a cushion or mattress having an adjustable depth of immersion;
a sensor comprising a sheet of conductive material;
a grounding plane being in the area around the sensor and allowing a capacitance measurement to be made relative to the distance between a person and the sensor;

a shield comprising a second sheet of conductive material located adjacent to and having generally the same shape and area as the sensor;

a circuit comprising a reference capacitor, the circuit adapted to
send short bursts of electrical current to the sensor and the reference capacitor,
measure the length of time the burst of current takes to charge the reference capacitor and the circuit adapted to calculate the relative proximity of the person based upon the time taken to charge the reference capacitor,
drive the shield to electrically isolate the shield from external capacitance or electromagnetic interference, and
provide an indication when the person is too deeply immersed within the cushion or mattress.

35. The immersion sensor assembly of claim 34 further comprising at least one layer of nonconductive material disposed over the sensor.

36. The immersion sensor assembly of claim 35 wherein the nonconductive material is foam.

37. The immersion sensor assembly of claim 34 wherein the sensor is disposed within a protective encasement.

38. The immersion sensor assembly of claim 34 wherein the device is integrally formed with a cushion.

39. The immersion sensor assembly of claim 34 wherein the device is integrally formed with a mattress.

40. The immersion sensor assembly of claim 34 wherein the planes formed by the sensor and the shield, when the immersion sensor is laid flat, are nominally parallel.

41. The immersion sensor assembly of claim 40 wherein the sensor comprises a plurality of sensors and the shield is sized to isolate the plurality of sensors.

42. The immersion sensor assembly of claim 41 wherein the circuit is attached to two or more of the plurality of sensors to simultaneously determine the proximity of people to each of the sensors.

43. The immersion sensor assembly of claim 42 wherein the circuit comprises a multiplexer, the multiplexer being attached to two or more of the sensors and also to the circuit and adapted to selectively connect the sensors to the circuit.

44. An immersion sensor for use with a cushion or mattress for measuring the depth of immersion of a person within the cushion or mattress comprising:
a sensor comprising a sheet of conductive material;
a ground layer comprising a second sheet of conductive material, the ground layer held at a constant ground electrical potential;
a shield comprising a second sheet of conductive material located adjacent to and having generally the same shape and area as the sensor;
a circuit for detecting the capacitance effect of an adjacent body and providing a relative output for a microcontroller; and
wherein the sensor and the shield, when the immersion sensor is laid flat, are nominally coplanar.

45. An immersion sensor assembly comprising:
an air mattress having an adjustable depth of immersion;
a sensor comprising a conductive material;
a ground comprising a second conductive material electrically isolated from the sensor and surrounding the sensor;
a circuit comprising a reference capacitor, the circuit adapted to send short bursts of electrical current to the sensor and the reference capacitor, the circuit adapted to measure the length of time the burst of current takes to charge the reference capacitor and the circuit adapted to calculate the proximity of a person based upon the time taken to charge the reference capacitor; and
wherein the circuit is adapted to provide an indication when the person is too deeply immersed within the air mattress.

46. A method of determining the proper immersion of a person within a cushion or mattress comprising the steps of:
providing a sensor layer below the cushion or mattress comprising a sheet of conductive material;
providing a ground layer that surrounds the sensor layer;
using the sensor to sense the proximity of the person to the sensor to determine the person's immersion within the cushion or mattress; and
generating a signal when the person is either overimmersed or underimmersed within the cushion or mattress.

* * * * *